United States Patent
Beger

Patent Number: 5,908,421
Date of Patent: Jun. 1, 1999

[54] SURGICAL DEVICE FOR FIXING BONE ELEMENTS

[75] Inventor: Jens Beger, Tuttlingen, Germany

[73] Assignee: Aesculap AG & Co. KG, Tuttlingen, Germany

[21] Appl. No.: 08/891,503

[22] Filed: Jul. 11, 1997

[30] Foreign Application Priority Data

Jul. 12, 1996 [DE] Germany .......................... 196 28 147

[51] Int. Cl.⁶ ................................................. A61B 17/56
[52] U.S. Cl. .............................. 606/61; 606/74; 606/201; 606/60; 606/59; 606/151
[58] Field of Search ................................. 606/61, 53, 54, 606/59, 60, 201, 202, 203, 74, 151

[56] References Cited

U.S. PATENT DOCUMENTS

| | | | |
|---|---|---|---|
| 3,910,280 | 10/1975 | Talonn | 606/203 |
| 4,667,662 | 5/1987 | Titone et al. | 606/74 |
| 5,395,374 | 3/1995 | Miller et al. | |

FOREIGN PATENT DOCUMENTS

| | | |
|---|---|---|
| 32 44 680 | 6/1984 | Germany . |
| 3244680 | 6/1984 | Germany . |
| 34 27 590 | 4/1987 | Germany . |
| 27 30 571 | 10/1987 | Germany . |
| 40 21 246 | 1/1992 | Germany . |
| 40 24 334 | 2/1992 | Germany . |
| 42 00 757 | 7/1992 | Germany . |
| WO 94/26192 | 11/1994 | WIPO . |
| WO 95/03002 | 2/1995 | WIPO . |
| WO 95/06438 | 3/1995 | WIPO . |

*Primary Examiner*—Michael Buiz
*Assistant Examiner*—(Jackie) Tan-Uyen Thi Ho
*Attorney, Agent, or Firm*—Barry R. Lipsitz; Ralph F. Hoppin

[57] ABSTRACT

In the case of a surgical device for fixing bone elements, having an elongated, flexible clamping means for winding around and bracing the bone elements to be fixed, having a connecting part for connecting the ends of the tightened clamping means, a first end of the clamping means being fastenable to the connecting part and the second free end of the clamping means being passable through an opening of the connecting part so as to form a loop, and having a locking member supported counter to the clamping direction against the connecting part and non-releasably connectable to the clamping means, in order to refine said device in such a way that, while being easy to handle, it not only enables a reliable permanent fixing of the clamping means but also, without additional aids, allows a temporary fixing during an operation, it is proposed that the locking member comprises a blocking element which blocks a movement of the clamping means counter to the clamping direction.

22 Claims, 2 Drawing Sheets

SURGICAL DEVICE FOR FIXING BONE ELEMENTS

BACKGROUND OF THE INVENTION

The invention relates to a surgical device for fixing bone elements, having an elongated, flexible clamping means for winding round and bracing the bone elements to be fixed, having a connecting part for connecting the ends of the tightened clamping means, a first end of the clamping means being fastenable to the connecting part and the second, free end of the clamping means being passable through an opening of the connecting part so as to form a loop, and having a locking member supported counter to the clamping direction against the connecting part and non-releasably connectable to the clamping means.

Such devices are used, in particular when setting oblique fractures of long bones, in the form of so-called cerclages where a clamping means, e.g. a wire loop or a metal strip, is wound round the bone elements to be fixed and then tensioned by means of a tensioning tool. The cerclages comprise a connecting part in the form of a cerclage clasp, by means of which the ends of the tensioned clamping means may be connected to one another. The cerclages are usually pre-fabricated by fastening a first end of the clamping means to the connecting part. The second, free end of the clamping means may be passed around the bone elements to be fixed, so as to form a loop, and then through an opening of the connecting part. The free end is then fixed to the connecting part.

The cerclages may be combined with additional osteosynthesis or internal fixation implants. Said option is used, for example, in surgery to the dorsal vertebral column. In the region of the thoracic and lumbar vertebrae, cerclages are used in conjunction with rod-shaped longitudinal supports for segmental correction and stabilization. To said end, the clamping means may be passed under the vertebral arches (sublaminar passage). Such methods are used, for example, for scoliosis, kyphosis, tumours and fractures. In the region of the cervical vertebrae, adjacent vertebral arches are connected by cerclages, e.g. in cases of fractures as well as post-traumatic and rheumatic instability. In many cases, sublaminar cerclages are also used in combination with screws and hook assemblies since, because the pedicle size in the thoracic vertebrae region decreases towards the head, a transpedicular screw fixation is no longer possible.

A basic requirement of such devices for fixing bone elements is that they should enable as simple as possible an operating technique, i.e. they should be easy to handle. A further important point is that over an extended period of time they should reliably exert a high clamping force upon the bone elements to be fixed. Since a plurality of cerclages are often used simultaneously, they should be designed in such a way as to allow first a temporary fixation during an operation so that a subsequent increase of the tension of the cerclages and a correction of the mutual position of the bone elements is possible.

To facilitate a subsequent increase of the tension of the cerclages, devices have already been proposed which operate on the principle of a cable binder (U.S. Pat. No. 4,667,662, WO 94/26192 as well as DE 27 30 571 C2) or a hose clip (DE 40 21 246 A1, DE 42 00 757 A1, DE 34 27 590 C2, DE 32 44 680 A1). In such systems, the clamping means comprises a tooth system, into which a corresponding pawl engages so that the cerclage is secured by means of a form-fit locking mechanism. The tooth system, however, poses a not inconsiderable risk of injury to the body tissue surrounding the bone elements to be fixed. Furthermore, although such refinements do guarantee a subsequent increase of the tension of the clamping element, a permanent fixation of the clamping means is not always guaranteed. Instead there is a danger of the clamping means loosening as time passes.

Cerclages are also known which use pressure clamps to fix the clamping means, a plurality of pressure clamps being threadable onto the clamping means. If, after tightening, the pressure clamp adjacent to the tensioning tool is first compressed, then after a readjustment of the tension the next pressing clamp inwards may be secured.

Such systems entail a relatively complex operating technique and the pressure clamps are easy to lose and difficult to manipulate.

Pressure clamps are also known which are permanently connected to the connecting part (WO 95/06438, U.S. Pat. No. 5,395,374, WO 95/03002). A temporary fixing is not possible with such refinements. To said end, additional clamps which are mountable onto the connecting part are provided, thereby making the operating technique not inconsiderably harder. The additional clamps moreover take up a substantial amount of room.

SUMMARY OF THE INVENTION

The object of the present invention is to refine a device for fixing bone elements of the type described in such a way that, while being easy to handle, it not only enables a reliable permanent fixing of the clamping means but also, without additional aids, allows a temporary fixing during an operation.

According to the invention, said object is achieved in a surgical device of the type described initially in that the locking member comprises a blocking element which blocks a movement of the clamping means counter to the clamping direction.

The blocking element allows the clamping means to be fixed at first temporarily during an operation, a readjustment of the tension being possible at any time because the blocking element merely blocks the movement of the clamping means counter to the clamping direction, a movement in clamping direction however remaining possible. Thus, additional aids are not needed for temporary fixing. In addition, by virtue of the locking member being supported counter to the clamping direction against the connecting part a permanent fixing is also enabled because the locking member, once a further readjustment of the tension is no longer required, is non-releasably connected to the clamping means. The locking member of the surgical device which is provided according to the present invention therefore enables both a permanent and a temporary fixing of the clamping means. Since the locking member is non-releasably connectable to the clamping means, the permanent fixing is of an extremely reliable design without entailing a complex operating technique. Before a permanent fixing is effected, the tension may be readjusted at any time by means of the blocking element without special aids having to be employed for said purpose.

It is particularly advantageous when the blocking element is integrally connected to the locking member. This enables a particularly space-saving refinement which is inexpensive to manufacture.

It is advantageous when the blocking element surrounds the clamping means in a peripheral direction because it is then possible to achieve a relatively large contact surface between clamping element and clamping means so that a movement of the clamping means counter to the clamping direction is reliably blocked.

It is particularly advantageous when the blocking element may be extensively applied, i.e. with surface contact, against the clamping means. Stress peaks exerted by the blocking element upon the clamping means and possibly leading to damage of the clamping means are thereby reduced.

In a particularly preferred embodiment of the invention it is provided that the opening of the connecting part takes the form of a through-hole and the blocking element comprises a clamping element, which engages counter to the clamping direction into the through-hole, widens in a wedge-shaped manner in clamping direction and is positionable between the wall of the through-hole and the surface of the clamping means. In such a refinement, the free end of the clamping means is passed through the through-hole of the connecting part. The wedge-shaped clamping element disposed between the wall of the through-hole and the surface of the clamping means acts as a friction locking mechanism which reliably prevents a movement of the clamping means counter to the clamping direction. Said property is utilized during temporary fixing. Owing to the friction between clamping means and clamping element, the latter in the event of a movement of the clamping means counter to the clamping direction is drawn into the through-hole of the connecting part and becomes wedged between the clamping means and the wall of the through-hole. A movement of the clamping means in clamping direction is however possible at any time because the clamping element upon a movement of the clamping means in clamping direction is displaced out of the through-hole of the connecting part and so the wedge formed by the clamping element does not exert any clamping force upon the clamping means.

In order to enlarge the contact surface between blocking element and clamping means, in a preferred embodiment it is provided that the blocking element comprises a plurality of clamping elements which surround the clamping means in a peripheral direction in the region of the through-hole. Here, it is particularly advantageous when the clamping elements are uniformly distributed over the periphery of the clamping means because then the clamping means, when it moves counter to the clamping direction, is acted upon by a clamping force uniformly over its periphery.

Upon a movement of the clamping means counter to the clamping direction, the clamping element as a result of the friction is drawn into the through-hole of the connecting part and so the clamping means becomes wedged. In order with only relatively low friction forces to guarantee reliable wedging, in a particularly preferred embodiment it is provided that the clamping element is elastically deformable in a radial direction of the through-hole. Consequently, even with relatively low friction forces the clamping element may adapt to the inside diameter of the through-hole and so is reliably drawn into the region between the surface of the clamping means and the wall of the though-hole.

In an inexpensive refinement of the blocking element it is provided that said element takes the form of a blocking sleeve, which surrounds the clamping means and engages counter to the clamping direction into the through-hole and of which the outside diameter widens conically in clamping direction.

Thus, when the surgical device is used, the free end of the clamping means is wound around the bone elements to be fixed and then passed through the through-hole of the connecting part and through the blocking sleeve. The conically constructed blocking sleeve then engages counter to the clamping direction into the region between the surface of the clamping means and the wall of the through-hole and, upon a movement of the clamping means counter to the clamping direction, is drawn by the friction force between clamping means and blocking sleeve into the through-hole so that the clamping means becomes wedged. A movement of the clamping means counter to the clamping direction is therefore reliably blocked.

It is advantageous when the blocking sleeve comprises a plurality of longitudinal slots because by said means the blocking sleeve is elastically deformable in a radial direction. The regions of the blocking sleeve between the individual longitudinal slots each form a clamping element of the type described above, the individual clamping elements being connected to one another by the unslotted region of the blocking sleeve.

It is advantageous when the blocking sleeve is made of a material with a relatively low modulus of elasticity, e.g. titanium. The blocking sleeve, made e.g. of titanium, because of the relatively low modulus of elasticity presents a high degree of elastic deformability and therefore adapts particularly easily to the inside diameter of the through-hole.

The tension readjustment of the surgical device is all the more reliable, the more sensitive the reaction of the blocking element to a movement of the clamping means counter to the clamping direction. This in turn is dependent upon the friction force required to draw the blocking sleeve into the through-hole of the connecting part. Said required friction force is considerably reduced when the through-hole widens conically in clamping direction, it being particularly advantageous when the conical form of the through-hole substantially corresponds to the conical form of the blocking sleeve which engages counter to clamping direction into the through-hole.

A further simplification of the operating technique when using the surgical device according to the invention is achieved in that the blocking member is captively connected to the connecting part.

For particularly reliable, permanent fixing, it is an advantage when the locking member fully surrounds the clamping means in a peripheral direction. This enables the formation of a particularly large contact area between locking member and clamping means and hence a reliable, permanent connection of the two parts. At the same time, pressure peaks exerted by the locking member upon the clamping means and possibly leading to damage and ultimately rupture of the clamping means are thereby avoided. The locking member may, for example, take the form of a locking sleeve which is compressible with the clamping means.

It is advantageous when the clamping means takes the form of a wire member, e.g. a wire cable, rope or line. Particularly in surgery to the vertebral column, e.g. in the case of sublaminar passage, there is only very little room available for application of the device according to the invention. The refinement of the clamping means in the form of a wire cable lends itself particularly well to such areas of application on account of its flexibility, dimensions and tensile strength.

In a particularly preferred embodiment of the device according to the invention, handling is facilitated in that a manually deformable guide tip is disposed in the region of the free end of the clamping means. With the aid of the guide tip, the clamping means may easily be introduced into the opening of the connecting part, and the guide tip prior to introduction may be manually deformed so that, even under confined spatial conditions, an easy application of the surgical device is enabled.

The introduction of the free end of the clamping means is further facilitated in that the diameter of the guide tip substantially corresponds to the diameter of the clamping means.

The following description of a preferred embodiment of the invention serves, in conjunction with the drawings, as a detailed explanation.

DETAILED DESCRIPTION OF THE INVENTION

Figure 1:
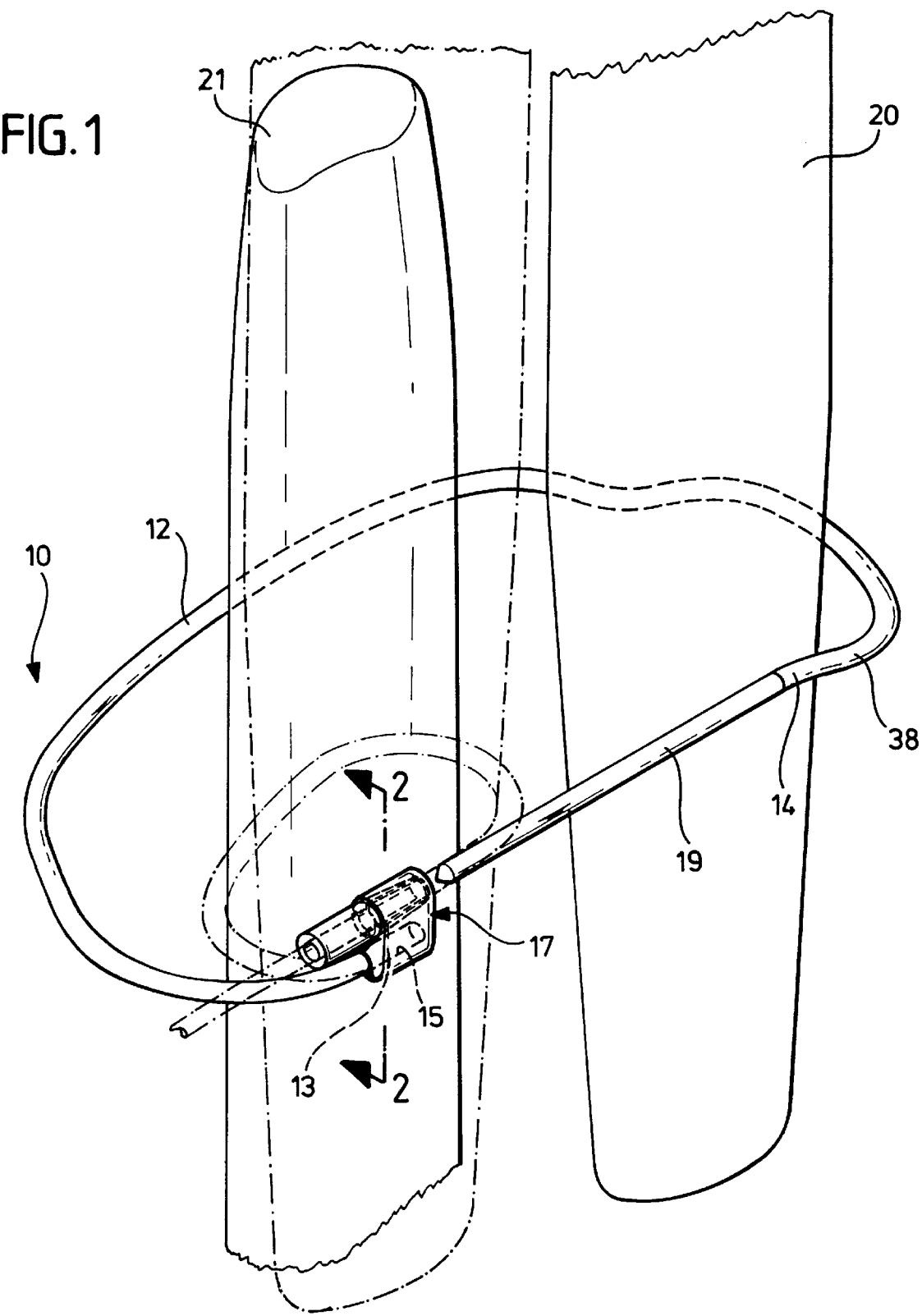
FIG. 1: a diagrammatic, perspective view of a surgical device for fixing bone elements according to the invention.

FIG. 1 shows a surgical device for fixing bone elements, which as a whole is provided with the reference character 10 and comprises a wire cable 12, the first end 13 of which is pressed into a cylindrical through-hole 15 of a connecting part 17 and to the second, free end 14 of which is connected a manually deformable guide tip 19, which facilitates introduction of the free end 14 through a conical hole 16 of the connecting part 17 extending parallel to the cylindrical through-hole 15.

The wire rope 12 forms a loop and encloses two oblong bone elements 20, 21, which together form a long bone which is fractured obliquely relative to its longitudinal extension. For surgical setting of the oblique fracture, the wire rope 12 is passed around the two bone elements 20 and 21 so as to form the loop, the free end 14 is then introduced by the guide tip 19 through the conical hole 16 of the connecting part 17 and then the wire rope 12 is tightened in the direction of the arrow 22 shown in FIG. 2, which symbolizes the clamping direction, in such a way that the two bone elements 20 and 21 are applied one against the other along the surface of the fracture.

Figure 2:
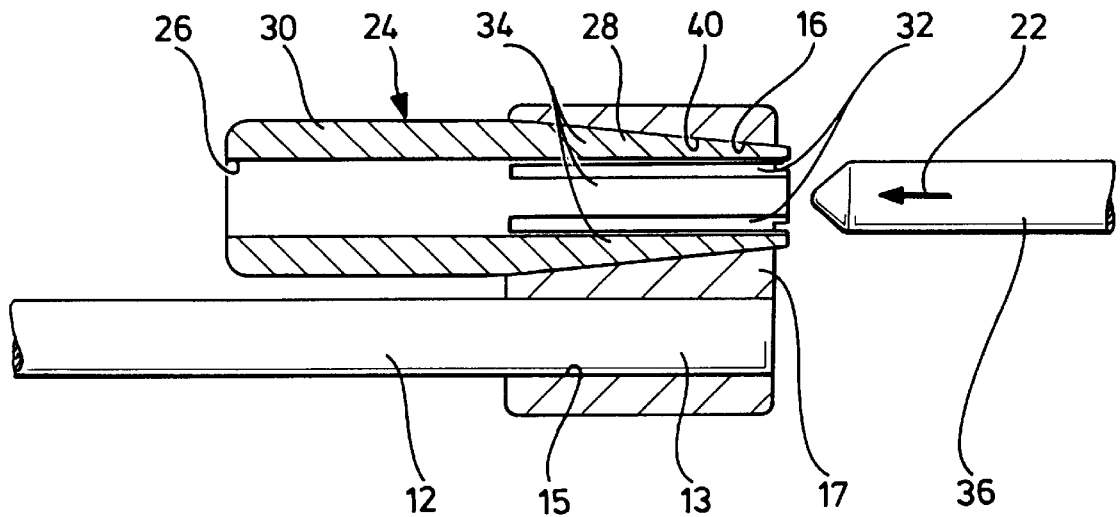
FIG. 2: a sectional view of the surgical device along the line 2—2 in FIG. 1 during introduction of the free end of the clamping means into the connecting part

As is evident particularly from FIG. 2, the conical hole 16 of the connecting part 17 is penetrated by a sleeve 24 having a longitudinal hole 26. The sleeve 24 comprises a conical portion 28, which is disposed inside the conical hole 16 and widens in clamping direction 22, and adjoining said portion in clamping direction a cylindrical portion 30 which projects beyond the connecting part 17. In a manner which will be explained below, the conical portion 28 forms a blocking element for the surgical device 10, while the sleeve 24 with its cylindrical portion 30 constitutes a locking member supported counter to the clamping direction 22 against the connecting part 17, blocking element and locking member being integrally connected to one another.

Since the longitudinal hole 26 is cylindrical and the conical hole 16 widens continuously in clamping direction in accordance with the outside diameter of the conical portion 28, the conical portion 28 in the sectional view shown in FIG. 2 presents a wedge-shaped form.

The conical portion 28 of the sleeve 24 is subdivided by longitudinal slots 32 extending in clamping direction 22 into a plurality of wedge-shaped clamps 34, which are distributed over the periphery of the sleeve 24 and integrally connected to one another by the unslotted cylindrical portion 30 of the sleeve 24. By virtue of the subdivision of the conical portion 28 into individual wedge-shaped clamps 34, the conical portion 28 is elastically deformable in a radial direction of the conical hole 16, i.e. the wedge-shaped clamps 34 act as individual spring elements which are disposed between the surface 36 of the guide tip 19 or the surface 38 of the free end 14 of the wire rope 12, on the one hand, and the wall 40 of the conical hole 16, on the other hand.

The conical portion 28 projects counter to the clamping direction 22 slightly beyond the connecting part 17 and through prying over, tamping or caulking is bent slightly outwards so that the sleeve 24 is held captive on the connecting part 17.

As described above, for application of the surgical device 10 the guide tip 19 and the free end 14 of the wire cable 12 are introduced through the longitudinal hole 26 of the sleeve 24 engaging into the conical bore 16, and then the wire cable 12 is tensioned with the aid of a conventional tensioning tool which is not shown in the drawings. The conical portion 28 of the sleeve 24 acts as a friction locking mechanism so that a movement of the clamped wire cable 12 counter to the clamping direction 22 is prevented. Said property is utilized during temporary fixing of the surgical device 10. Prevention of a movement of the clamped wire cable 12 counter to the clamping direction 22 is effected in that, as a result of the friction between the wire cable 12 and the sleeve 24, the conical portion 28 upon a movement of the wire cable 12 counter to the clamping direction 22 is drawn into the conical hole 16 of the connecting part 17. The result is that the slotted conical portion 28 at its end remote from the cylindrical portion 30 is radially compressed and so the wire cable 12 becomes wedged. Whereas a movement of the wire cable 12 counter to the clamping direction 22 is thereby reliably prevented, a movement in the opposite direction is possible at any time because, in said case, the end of the conical portion 28 remote from the cylindrical portion 30 of the sleeve 24 widens as far as possible so that the wire cable 12 may be passed unimpeded in clamping direction 22 through the longitudinal hole 26 of the sleeve 24. A readjustment of the tension of the surgical device 10 is therefore possible without difficulty.

Figure 3:
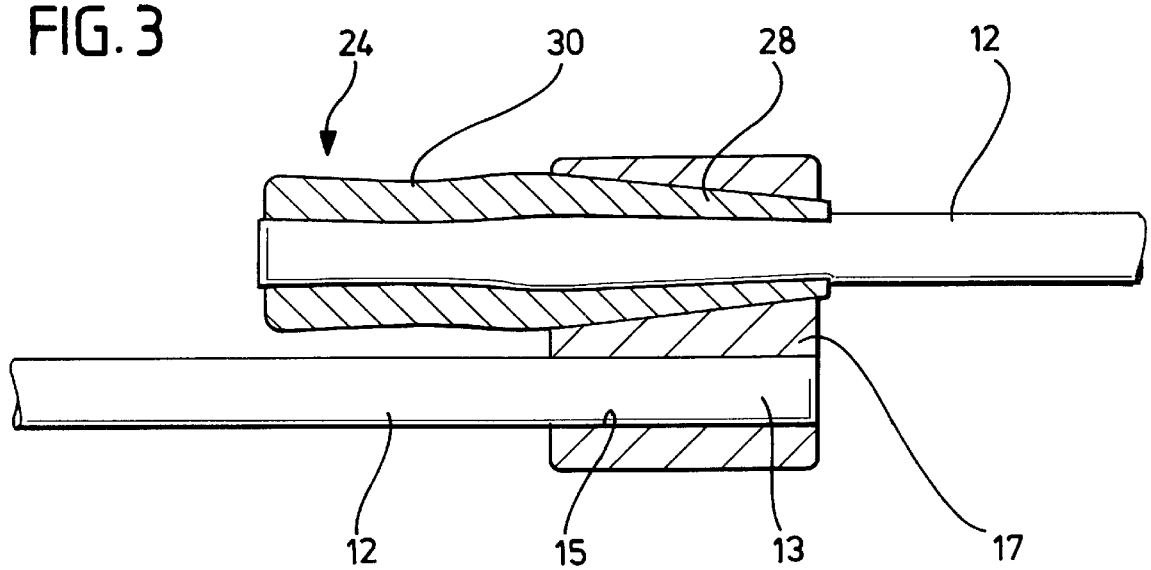
FIG. 3: a sectional view corresponding to FIG. 2 after the ends of the clamping means have been permanently fixed.

For final fixing, using known forceps which are suitable for said purpose the cylindrical portion 30 is radially compressed in the manner illustrated diagrammatically in FIG. 3. As a result, even when relieved of tension, the wire cable 12 is reliably secured in the surgical device 10. Under renewed tension, the conical portion 28 is again drawn into the conical hole 16 of the connecting part 17 and the wire cable 12 is additionally secured by means of the friction locking mechanism. Under tension, the cylindrical portion 30 of the sleeve 24 compressed with the wire cable 12 therefore only has to absorb a reduced amount of the tensile forces so that a sliding of the wire cable 12 out of the compressed cylindrical portion 30 is reliably prevented. Rather, the compressed cylindrical portion 30 substantially serves merely as a safeguard in case the surgical device is relieved of tension, in the form of a safeguard against loss. This is advantageous particularly because, when using materials with a low modulus of elasticity such as, for example, titanium, the cylindrical portion 30 upon compression springs back slightly. In known constructions, this has proved a serious drawback. Since however, when using materials with a relatively low modulus of elasticity such as, for example, titanium, the wedge-shaped clamps 34 of the conical portion 28 serving as spring elements may adapt more easily to the wall 40 of the conical hole 16 and then reliably clamp the wire cable 12, in the surgical device according to the invention it is possible, for example, also to use titanium without impairing the fixing of the ends of the wire cable 12.

What is claimed is:

1. A surgical device for fixing bone elements, comprising:
   an elongated, flexible clamping means with a first end and a second, free end for winding around and bracing bone elements to be fixed,
   a connecting part for connecting the ends of the tightened clamping means,
   the first end of the clamping means being fastenable to the connecting part,
   the second, free end of the clamping means being passable through an opening of the connecting part so as to form a loop, and
   a locking member supported counter to a clamping direction against the connecting part and non-releasably connectable to the clamping means,
   wherein:
     the locking member comprises a blocking element that is positionable relative to the connecting part in a non-blocking position and in a blocking position,
     in the blocking position, the blocking element blocks a movement of the clamping means counter to the clamping direction to secure the clamping means to the connecting part, and
     in the non-blocking position, the blocking element allows the clamping means to move essentially unimpeded with respect to the connecting part in the clamping direction.

2. A surgical device according to claim 1, wherein:
   the blocking element is integrally connected to the locking member.

3. A surgical device according to claim 1, wherein:
   the blocking element surrounds the clamping means in a peripheral direction.

4. A surgical device according to claim 1, wherein:
   the blocking element is extensively appliable against the clamping means.

5. A surgical device according to claim 1, wherein:
   the opening of the connecting part takes the form of a though-hole, and
   the blocking element comprises a clamping element, which engages counter to the clamping direction into the through-hole, widens in a wedge-shaped manner in the clamping direction and is positionable between a wall of the through-hole and a surface of the clamping means.

6. A surgical device according to claim 5, wherein:
   the blocking element comprises a plurality of clamping elements which surround the clamping means in a peripheral direction in a region of the through-hole.

7. A surgical device according to claim 5, wherein:
   the clamping element is elastically deformable in a radial direction of the through-hole.

8. A surgical device according to claim 5, wherein:
   the blocking element takes the form of a blocking sleeve, which surrounds the clamping means and engages counter to the clamping direction into the through-hole and of which the outside diameter widens conically in the clamping direction.

9. A surgical device according to claim 8, wherein:
   the blocking sleeve comprises a plurality of longitudinal slots.

10. A surgical device according to claim 8, wherein:
    the blocking sleeve comprises titanium.

11. A surgical device according to claim 1, wherein:
    the through-hole widens conically in the clamping direction.

12. A surgical device according to claim 1, wherein:
    the blocking element is captively connected to the connecting part.

13. A surgical device according to claim 1, wherein:
    the locking member surrounds the clamping means in a peripheral direction.

14. A surgical device according to claim 13, wherein:
    the locking member comprises a locking sleeve which is compressible with the clamping means.

15. A surgical device according to claim 1, wherein:
    the clamping means comprises a wire member.

16. A surgical device according to claim 1, wherein:
    a manually deformable guide tip is disposed in a region of the second, free end of the clamping means to allow the guide tip to be easily introduced into the opening of the connecting part.

17. A surgical device according to claim 16, wherein:
    a diameter of the guide tip substantially corresponds to a diameter of the clamping means.

18. A surgical device according to claim 1, wherein:
    the blocking element achieves its blocking position when it is moved relative to the connecting part in a direction that is counter to the clamping direction until it engages the connecting part such that a radially inward pressure is exerted on the clamping means to secure the clamping means to the connecting part, and
    the blocking element achieves its non-blocking position when it is moved relative to the connecting part in the clamping direction until it disengages the connecting part such that the radially inward pressure is released to allow the clamping means to move freely in the clamping direction, unimpeded by the connecting part.

19. A surgical device according to claim 1, wherein:
    in the non-blocking position, the blocking element allows the clamping means to move freely with respect to the connecting part in the clamping direction to allow a readjustment of a tension of the clamping means.

20. A surgical device according to claim 6, wherein:
    the plurality of clamping elements comprise elongated spring elements for clamping the clamping means in the through-hole when the blocking element is in its blocking position.

21. A surgical device for fixing bone elements, comprising:
    an elongated, flexible clamping means with a first end and second, free end for winding around and bracing bone elements to be fixed,
    a connecting part for connecting the ends of the tightened clamping means,
    the first end of the clamping means being fastenable to the connecting part,
    the second, free end of the clamping means being passable through an opening of the connecting part so as to form a loop, and
    a locking member supported counter to a clamping direction against the connecting part, wherein:
      the locking member comprises a blocking element that is positionable relative to the connecting part in a non-blocking position and in a blocking position,
      in the blocking position, the blocking element blocks a movement of the clamping means counter to the clamping direction to secure the clamping means to the connecting part, and in the non-blocking position, the blocking element allows the clamping means to move essentially unimpeded with respect to the connecting part.

22. A surgical device for fixing bone elements, comprising:

a connecting part for connecting the ends of an elongated, flexible clamping means for winding around and bracing bone elements to be fixed, said connecting part comprising means for fastening a first end of the clamping means thereto, said connecting part comprising an opening through which a second, free end of the clamping means is passable, and a locking member supported counter to a clamping direction against the connecting part, wherein:

the locking member comprises a blocking element that is positionable relative to the connecting part in a non-blocking position and in a blocking position, in the blocking position, the blocking element is adapted to block a movement of the clamping means counter to the clamping direction to secure the clamping means to the connecting part, and in the non-blocking position, the blocking element is adapted to allow the clamping means to move essentially unimpeded with respect to the connecting part.

* * * * *